United States Patent [19]

Znotins et al.

[11] 4,182,716

[45] Jan. 8, 1980

[54] METHOD OF MAKING 5,6-DIHYDRO-2-METHYL-N-PHENYL-1,4-OXATHIIN-3-CARBOXAMIDE

[75] Inventors: Andrew A. Znotins, Guelph; Arthur D. Brewer, Puslinch, both of Canada

[73] Assignee: Uniroyal, Ltd., Ontario, Canada

[21] Appl. No.: 958,909

[22] Filed: Nov. 8, 1978

[30] Foreign Application Priority Data

Sep. 5, 1978 [CA] Canada ................................ 310616

[51] Int. Cl.² ............................................. C07D 327/06
[52] U.S. Cl. ..................................... 549/14; 424/276; 549/30; 549/40
[58] Field of Search ................................. 260/327 P

[56] References Cited

U.S. PATENT DOCUMENTS

| | | | |
|---|---|---|---|
| 3,005,852 | 10/1961 | Freyermuth et al. ................. | 260/607 |
| 3,006,963 | 10/1961 | Buc et al. ............................. | 260/607 |
| 3,249,499 | 5/1966 | Von Schmeling et al. ... | 260/327 P X |
| 3,393,202 | 7/1968 | Kulkla et al. ....................... | 260/327 P |
| 3,882,237 | 5/1975 | Knight et al. ......................... | 424/276 |

FOREIGN PATENT DOCUMENTS

| | | | |
|---|---|---|---|
| 1035778 | 8/1978 | Canada ................................ | 260/327 P |
| 1036167 | 8/1978 | Canada ................................ | 260/327 P |
| 1335626 | 10/1973 | United Kingdom ............. | 260/607 AL |

OTHER PUBLICATIONS

Djerassi et al., J. Am. Chem. Soc., vol. 75, pp. 3704–3708 (1953).
Janssen et al., J. Org. Chem., vol. 42, pp. 1530–1533 (1977).
Wilson, J. Am. Chem. Soc., vol. 87, pp. 3785–3786 (1965).
Breslow et al., Multi-Sulfur and Sulfur and Oxygen Five- and Six-Membered Heterocycles, Part Two, pp. 816 to 825, Interscience Publishers, 1966 (NY).

*Primary Examiner*—John D. Randolph
*Attorney, Agent, or Firm*—James J. Long

[57] ABSTRACT

This method of making 5,6-dihydro-2-methyl-N-phenyl-1,4-oxathiin-3-carboxamide is based on the use of an oxathiolane, namely, 2-methyl-N-phenyl-1,3-oxathiolane-2-acetamide, which may be formed by condensing 2-mercaptoethanol with acetoacetanilide under acidic conditions in a solvent medium (aromatic hydrocarbon, chlorinated hydrocarbon or alkyl ester of an aliphatic acid). The said oxathiolane, with or without purification, is reacted with hydrogen peroxide in water or in a water-organic solvent mixture under basic conditions in the presence of a catalytic amount of a metal compound such as sodium tungstate to form 2-methyl-N-phenyl-1,3-oxathiolane-2-acetamide 3-oxide. The said oxathiolane oxide, while dissolved in a chlorinated hydrocarbon or an alkyl ester of an aliphatic carboxylic acid, or while suspended in an aromatic hydrocarbon, is subjected to a ring expansion reaction by heating under acidic conditions in the presence of a catalytic quantity of a quaternary ammonium salt to form 5,6-dihydro-2-methyl-N-phenyl-1,4-oxathiin-3-carboxamide with evolution of water. The product is a known bactericide and fungicide.

21 Claims, No Drawings

METHOD OF MAKING 5,6-DIHYDRO-2-METHYL-N-PHENYL-1,4-OXATHIIN-3-CARBOXAMIDE

This invention relates to a method of making 5,6-dihydro-2-methyl-N-phenyl-1,4-oxathiin-3-carboxamide, which is a known bactericide and fungicide.

The method of the invention involves the use of an oxathiolane intermediate [formed by condensing mercaptoethanol (I) with acetoacetanilide (II) under acidic conditions to form the intermediate 2-methyl-N-phenyl-1,3-oxathiolane-3-acetamide (III)] which is then oxidized under basic conditions to its 3-oxide (IV), and thereafter converted by a ring expansion reaction under acidic conditions to 5,6-dihydro-2-methyl-N-phenyl-1,4-oxathiin-3-carboxamide (V), according to the following equations:

Step A

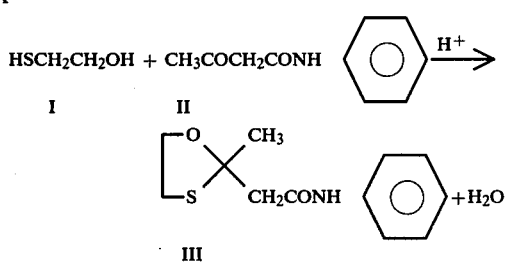

Step B

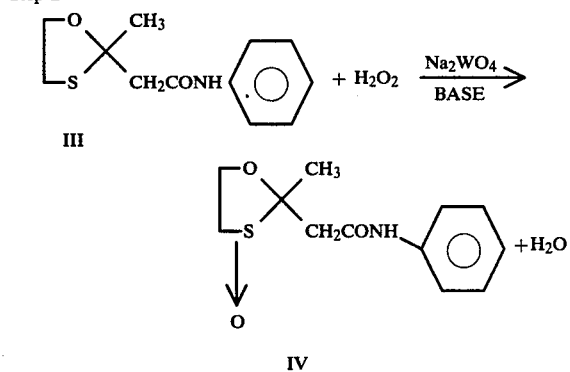

Step C

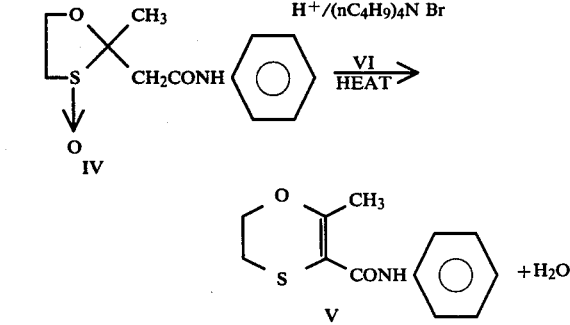

U.S. Pat. No. 3,393,202, July 18, 1968, Kulka et al, discloses conventional methods for making 5,6-dihydro-2-methyl-N-phenyl-1,4-oxathiin-3-carboxamide, involving the use of chlorinating agents and producing noxious by-products which are ecologically undesirable.

Canadian Pat. No. 1,036,167, W. S. Lee, Aug. 8, 1978, discloses synthesis of dihydro-1,4-oxathiins by rearrangement of 1,3-oxathiolane sulfoxides. The present invention provides an improved process.

The invention is concerned with a method of making 5,6-dihydro-2-methyl-N-phenyl-1,4-oxathiin-3-carboxamide comprising the steps of:

(A) providing an intermediate oxathiolane, preferably by bringing together 2-mercaptoethanol and acetoacetanilide in at least one organic solvent selected from the group consisting of (a) aromatic hydrocarbon solvent, (b) chlorinated hydrocarbon solvent, and (c) a solvent which is an alkyl ester of an aliphatic acid, in the presence of a catalytic quantity of a dehydrating acid, and heating the resulting mixture at a temperature of 45°–70° C. while removing evolved water of reaction, whereby 2-methyl-N-phenyl-1,3-oxathiolane-2-acetamide is formed;

(B) bringing together the 2-methyl-N-phenyl-1,3-oxathiolane-2-acetamide and hydrogen peroxide under basic conditions in the presence of a catalytic quantity of a heavy metal compound, in a medium comprising water, or water plus organic solvent as defined in step (A) above, whereby 2-methyl-N-phenyl-1,3-oxathiolane-2-acetamide 3-oxide is formed;

(C) bringing together the 2-methyl-N-phenyl-1,3-oxathiolane-2-acetamide 3-oxide and a catalytic quantity of a quaternary ammonium compound under acidic conditions in organic solvent as defined in step (A) above, and heating the mixture at a temperature of 45°–80° C., while removing evolved water of reaction, and thereafter recovering from the reaction mixture the thus formed 5,6-dihydro-2-methyl-N-phenyl-1,4-oxathiin-3-carboxamide.

The 2-methyl-N-phenyl-1,3-oxathiolane-2-acetamide (III) intermediate formed in Step A can be purified and isolated, but is preferably converted directly to the corresponding 2-methyl-N-phenyl-1,3-oxathiolane-2-acetamide 3-oxide (IV) by the action of aqueous hydrogen peroxide in Step B. This oxidation is carried out under basic conditions in the presence of catalytic quantities of a heavy metal compound such as sodium tungstate in an effective mixture of a suitable organic solvent and water or water alone.

The oxathiolane oxide (IV) is converted, preferably without isolation or purification, to the oxathiin (V) in Step C by a thermal ring expansion reaction carried out in a suitable solvent under acidic conditions in the presence of catalytic quantities of a quaternary ammonium compound such as tetra n-butyl ammonium bromide. In the absence of the quaternary ammonium compound the reaction proceeds at a slower rate and the yields are markedly lower due to decomposition of IV.

Suitable nonprotic solvents which can be used individually, or possibly in combinations, for individual stages or the entire reaction sequence are:

(a) aromatic hydrocarbons having a boiling point not greater than 145° C., e.g. benzene, toluene, xylene;
(b) chlorinated hydrocarbons having a boiling point not greater than 130° C., e.g., chloroform;
(c) solvents having a boiling point not greater than 130° C. which are alkyl esters of aliphatic acids, e.g., isopropyl acetate or n-butyl acetate.

The preferred solvent is toluene. Benzene is toxic and is not preferred.

The phenyl group of the starting compound (and consequently of the final product) may be substituted if desired with one or more non-interfering substituents, such as at least one lower alkyl or lower alkoxy substituent.

The present process is highly advantageous compared to certain other proposed processes which require multiple changes of solvent with associated losses and increased pollution control burden. The necessity of constant solvent change also results in a labor intensive and expensive process. By contrast the present process can be carried out entirely in the same medium or at most involves only the change from toluene to methylene chloride/toluene and back to toluene, for example. It does not involve any expensive and difficult to remove dimethylformamide (boiling point about 153° C.). Certain prior processes involving the use of benzene (a toxic solvent) depend upon a co-solvent (dimethylformamide) without which extensive decomposition of the oxathiolane 3-oxide occurs, with resultant low yields of oxathiin (V).

Certain proposed processes, as described in the above-cited Canadian Pat. No. 1,036,167 of Lee, are relatively non-productive in that they involve working in dilute solutions which result in small quantities of product made in any one run. Furthermore the cycle times involved are so long as to render the productivity uneconomic. By contrast the present process is operable in high concentration and short reaction times so that productivity more than 40 times greater is possible.

The present method of obtaining the oxathiolane oxide (IV) avoids the use of acetic acid, a protic solvent, and thus offers the following advantages: (1) a non-productive solvent change is avoided; (2) there are no costs for acetic acid, caustic soda to neutralize this acid, nor for disposal of the resulting sodium acetate in an ecologically sound manner. By contrast, the nonprotic solvent system employed in the present invention allows the use of hydrogen peroxide alone catalyzed by traces of heavy metal compound such as sodium tungstate which is readily recyclable giving only water as by-product.

The present process involves the use of various quaternary ammonium compounds as effective catalysts in the formation of the oxathiin (V) in Step C. These catalysts can be used in minute quantities. Certain other processes do not involve the use of catalysts other than p-toluene-sulfonic acid but instead involve a mixture of solvents with dimethylformamide which is expensive and difficult to recover because of its high boiling point.

In typical practice of Step A of the invention, acetoacetanilide (II) is reacted with 2-mercaptoethanol (I) in one of three types of solvents: (a) aromatic hydrocarbons, e.g., toluene (b) chlorinated hydrocarbons, e.g., chloroform (c) alkyl esters of aliphatic acids, e.g., isopropyl acetate or n-butyl acetate. Typically, between 0.5-6 liters of solvent may be used per kilogram of reactants [acetoacetanilide (II)+2-mercaptoethanol (I)]. Trace amounts (e.g., 0.5-8% by weight of reactants) of acid dehydration promoter such as p-toluenesulfonic acid or 2-naphthalenesulfonic acid may be used to catalyze the reaction. The relative proportions of acetoacetanilide and 2-mercaptoethanol are not critical; equimolar or approximately equimolar proportions are suitable but an excess of one or the other of the reactants may also be present. Frequently it is advantageous to use a slight excess of 2-mercaptoethanol.

The reaction between the acetoacetanilide and the 2-mercaptoethanol is preferably carried out at a temperature of 45°-70° C. For convenience in removing the water of reaction, it is preferable to reflux the reaction mixture during the process. With most of the solvents employed, this means conducting the reaction under reduced pressure, except when the solvent is chloroform which boils at about 60° C.

Reaction temperatures greater than about 70° C. are deleterious to yield due to side reactions. The reaction time frequently varies from 2 to 8 hours.

At the conclusion of the reaction between I and II two alternatives are possible. Alternative (i), which is preferred, comprises the conversion of the oxathiolane (III) in the reaction mixture directly to oxathiolane oxide (IV) in Step B without purification. A direct conversion is usually the most productive sequence. Toluene is frequently the preferred solvent.

Alternative (ii), which involves purification, ordinarily requires a change of solvents prior to oxidation of oxathiolane (III) to oxathiolane oxide (IV) in Step B. It typically comprises a base wash (e.g., saturated aqueous sodium bicarbonate solution), phase separation, drying over a desiccant (e.g., magnesium sulfate), filtration and reduction in volume. To achieve high yields a diluent (e.g., toluene, methylene chloride) is ordinarily added prior to the base wash if the solvent of choice is toluene and less than 2 liters of toluene per kilogram of reactants were used to carry out the condensation reaction.

Step B, the conversion of oxathiolane (III) to oxathiolane oxide (IV), is accomplished by a heterogeneous reaction with aqueous hydrogen peroxide in an effective mixture of a suitable organic solvent (i.e., as previously described) and water or water alone. The exact proportions of solvent, water and oxathiolane (III) are not critical and may vary considerably depending upon the solubility of oxathiolane (III) in the organic solvent. It will be understood that the amount of organic solvent that is most appropriate ordinarily varies inversely with the solubility of oxathiolane (III) in that organic solvent. Thus, to complete the oxidation about 0.6 liter chloroform per kilogram of oxathiolane (III) might be used versus about 1-1.5 liters toluene per kilogram of oxathiolane (III). In any event, there will ordinarily not be more than about 4 liters (e.g., 0.5-4 liters) of liquid medium (water, or water plus solvent), preferably not more than about 2 liters, present per kilogram of oxathiolane in this oxidation step. Usually the liquid medium comprises at least 10% water by weight.

The pH of the aqueous phase in Step B must be maintained at greater than 7 and preferably in the range of 8-9. This suppresses the reversion of oxathiolane (III) to the starting materials I and II. Any appropriate base may be used to control the pH, including the organic and inorganic bases, of which particularly convenient suitable examples are sodium bicarbonate, sodium acetate, sodium formate and sodium hydroxide. The required amount of the base is conveniently dissolved in one liter of water per four kilograms of oxathiolane oxide (IV). When Alternative (ii) (Step A) is followed, it is advantageous to use saturated (6-8% by weight) sodium bicarbonate solution [1 liter per 4 kilograms of oxathiolane oxide (IV)]. When Alternative (i) (Step A) is followed additional base (e.g., sodium hydroxide) is appropriately added to compensate for the p-toluenesulfonic acid used as catalyst in Step A.

The oxidation step is carried out with the aid of a heavy metal compound oxidation catalyst, notably a metal (including alkali metal and alkaline earth metal), ammonium or amine salt of tungstic or molybdic acid, or a zirconium compound, especially a zirconium salt, such as zirconium tetrachloride or zirconium tetranitrate. The preferred catalysts are the metal salts of tungstic and molybdic acid. The most preferred catalyst is sodium tungstate. Catalytic concentrations are usually about 0.1 or less to 2 or more percent by weight based on the weight of the oxathiolane. Without such a catalyst the reaction proceeds only slowly or not at all in the media described above.

The oxidation step is carried out with very vigorous stirring at temperatures ranging from 0°–25° C. approximately. Since the reaction is exothermic, cooling is appropriate in the early stages. Control of the reaction is facilitated by gradual addition of the oxidizing agent, so as to avoid an excessive exotherm, particularly at the start. It is particularly advantageous to carry out the Step B reaction in two stages; in the first stage, which typically lasts 1 to 3 hours, the temperature is ordinarily maintained at 0°–10° C., while in the second stage, which also commonly lasts 1 to 3 hours, the temperature may be permitted to rise into the upper end (e.g., 20°–25° C.) of the reaction temperature range. Slow addition of 35% hydrogen peroxide (other commercial grades, e.g., 30–70% may be used) is carried out during the initial part of the first stage (e.g., on a laboratory scale, dropwise addition over a period of 10 to 30 minutes). Ordinarily an amount of peroxide approximately equivalent to (usually slightly in excess of) the oxathiolane (III) is used.

A simple phase separation completes the reaction sequence in the cases where the solvent of choice is either a chlorinated hydrocarbon or an alkyl ester of an aliphatic acid. A quantity of methylene chloride (ordinarily the minimum quantity necessary to achieve a two-phase system, e.g., 10–100% by volume of the reaction mixture) is appropriately added when the solvent of choice is an aromatic hydrocarbon. In any case, the aqueous phase is discarded or recycled (to recover sodium tungstate). The organic phase is dried over a desiccant (e.g., magnesium sulfate) or by azeotropic distillation of a portion of the solvent to remove the water present. In the cases where the solvent of choice is either a chlorinated hydrocarbon or alkyl ester of an aliphatic acid the dried solutions are suitable for Step C. The toluene/methylene chloride/oxathiolane oxide (IV) solution is reduced in volume to remove the methylene chloride present to make oxathiolane oxide (IV) suitable for Step C. If desired, this reduction in volume of the toluene/methylene chloride/oxathiolane oxide (IV) solution may be combined with the initial step of Step C.

Oxathiolane oxide (IV) prepared by the sodium tungstate/hydrogen peroxide method is a heat sensitive syrup ordinarily consisting of a mixture of cis/trans isomers typically in the ratio of about 2:1 respectively. Oxathiolane oxide (IV) readily undergoes decomposition at temperatures greater than about 50° C. or in the presence of acids; therefore, all reductions in volume are appropriately carried out at reduced pressures under neutral or slightly basic conditions.

To carry out Step C oxathiolane oxide (IV) is dissolved (if not already in solution) in a suitable solvent consisting essentially of either a chlorinated hydrocarbon or an alkyl ester of an aliphatic acid or suspended in a medium consisting essentially of an aromatic hydrocarbon usually in an amount ranging for example from 1–12 liters of solvent per kilogram of oxathiolane oxide (IV). An effective mixture of a dehydrating acid (e.g., p-toluenesulfonic acid, methanesulfonic acid, phosphoric acid or 2-naphthalenesulfonic acid) and a quaternary ammonium salt, particularly a quaternary ammonium halide, is added. Typical quaternary ammonium halides may be represented by the formula

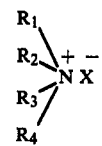

where X is halogen (fluorine, chlorine, bromine or iodine) and $R_1$, $R_2$, $R_3$ and $R_4$ are the same or different and may be for example alkyl (usually $C_1$–$C_{16}$), phenyl (unsubstituted or substituted with a noninterfering substituent), benzyl, etc. Most preferred are tetrabutylammonium bromide, tetrapentylammonium iodide and trimethylphenylammonium bromide. Ordinarily initial quantities of the dehydrating agent and quaternary ammonium salt are employed in weight ratio of about 1:20 but other ratios are suitable. Remarkably small quantities [e.g., 0.25 percent or less to 3 percent or more, by weight based on the oxathiolane oxide (IV)] are effective. The resulting solution (suspension) is subjected to a moderately elevated temperature, sufficient to cause the reaction to proceed at a reasonable rate but not so high as to cause decomposition. A reaction temperature of 40°–80° C. is usually satisfactory. The water formed as the reaction proceeds is removed in a suitable manner, for example by refluxing under a separating device such as a Dean and Stark trap. Such refluxing may be performed under reduced pressure to avoid heating to an excessive temperature. A typical refluxing temperature range is 45°–50° C. An additional amount of p-toluenesulfonic acid [e.g., one percent by weight of oxathiolane oxide (IV)] is typically added and refluxing is continued for an hour or so at 45°–50° C., followed by a longer period (e.g., 2 to 4 hours) of refluxing at a higher temperature (e.g., 75°–80° C., except when chloroform [which boils at about 60° C.] is used). About 30% of the water of reaction is generated in the initial state, the remainder at the elevated temperature. It may be advantageous to wash the reaction mixture with dilute acid (e.g., hydrochloric acid) just prior to the final heating stage. The solution is cooled to about 20° C., washed with an aqueous 10% sodium hydroxide solution [about 200 ml per gram mole of oxathiolane (III)], and the organic phase dried over a desiccant (e.g., magnesium sulfate) and reduced in volume under vacuum. The residue is then typically recrystallized from a suitable solvent, usually either cold toluene or cold isopropyl alcohol (e.g., 3 ml of solvent per gram of residue). The preferred method is to carry out the reaction sequence in toluene, wash with base, cool the toluene layer to precipitate the oxathiin (V), filter, and dry.

Typical cycle times (actual reaction time excluding time for manipulations such as solvent removal, phase separations, etc.) are as follows:

| Step | Cycle Times (Hours) | | |
|---|---|---|---|
| | Broad | Preferred | Most Preferred |
| A | 1–10 | 2–6 | 2–4 |
| B | 1–6 | 1–4 | 1–3 |
| C | 2–15 | 2–10 | 2–7 |

The major gain in productivity made possible by the invention is realized particularly in Step C. This may be demonstrated by considering the above-cited Canadian Pat. No. 1,036,167 of Lee, Example 5, which discloses a reaction time of at least 33 hours coupled with a dilution factor of 40 ml solvent per gram of reactant. Lee's overall yield based on acetoacetanilide is 71.5% (Example 1: 90.2%; Example 3: 93.33%, Example 5: 85%). Compare this with the best yield disclosed in the following examples, namely, 63% based on acetoacetanilide with reaction times of 7 hours coupled with a dilution factor of 4 ml solvent per gram of reactants, on which basis the present productivity is about 41 times that of Lee.

The following examples will serve to illustrate the practice of the invention in more detail.

EXAMPLE 1

A mixture of toluene (1200 ml), p-toluenesulfonic acid monohydrate (12 g), 2-mercaptoethanol (330 g, 4.225 moles) and acetoacetanilide (709.2 g, 4 moles) is refluxed under a Dean and Stark trap for 5.5 hours at 60°–65° C. at a pressure of about 140 mm Hg. The reaction mixture is cooled to 25° C., methylene chloride added (1000 ml), and the resulting solution washed with aqueous saturated sodium bicarbonate solution (400 ml). The organic layer is separated, dried over magnesium sulfate, filtered, and reduced in volume under vacuum. Yield 936 g (98.6%) of oxathiolane (III).

A mixture of oxathiolane (III) (48.8 g, 0.205 mole) (prepared above), toluene (73.2 ml), saturated sodium bicarbonate (10.2 ml) and water (2 ml) containing sodium tungstate dihydrate (0.19 g), is stirred vigorously and treated dropwise with hydrogen peroxide (19.9 ml, 0.215 mole) at 0°–5° C. The mixture is stirred for 2 hours at 0°–5° C., and for 2 hours at 20°–25° C. A minimum (175 ml) of methylene chloride is added to achieve a two-phase system. The aqueous phase is separated and washed with a small portion of methylene chloride. The organic layers are combined, dried over magnesium sulfate, and reduced in volume under vacuum.

A mixture of crude oxathiolane oxide (IV) (prepared above), toluene (191.2 ml), tetra n-butyl ammonium bromide (0.956 g), and p-toluenesulfonic acid monohydrate (0.047 g) is heated at reflux under a Dean and Stark trap at 50° C. at a pressure of about 80 mm Hg for 3 hours. Additional p-toluenesulfonic acid monohydrate (0.72 g) is added and the solution refluxed for 1 hour at 50° C. followed by reflux at 80° C. for 3 hours. The reaction mixture is cooled and washed with aqueous 10% sodium hydroxide solution (20 ml) and water (20 ml). The organic phase is separated, dried over magnesium sulfate, filtered and reduced in volume under vacuum. Crystallization from isopropyl alcohol gives a first crop yield of 31 g, 63% of oxathiin (V) based on acetoacetanilide (II).

EXAMPLE 2

Toluene (600 ml), p-toluenesulfonic acid monohydrate (4 g), 2-mercaptoethanol (78 ml, 1.1 moles, distilled), and acetoacetanilide (177 g, 1 mole) are heated at reflux under a Dean and Stark trap for 5¼ hours at 50°–55° C. at a pressure of about 120 mm Hg. The solution is cooled to 20°–23° C. and washed with saturated sodium bicarbonate solution (100 ml). The organic layer is separated, dried over magnesium sulfate, filtered and reduced in volume under vacuum. Yield 234.8 g of oxathiolane (III) (98.9% based on acetoacetanilide).

Oxathiolane (III) (35.6 g, 0.15 mole) (prepared above), toluene (110 ml), water (10 ml), sodium formate (0.6 g) and sodium tungstate dihydrate (0.35 g) are stirred vigorously and treated dropwise with hydrogen peroxide (13.6 ml, 34.1%, 0.155 mole) at 0°–4° C. over 10 minutes. The solution is stirred for a further 2 hours in an ice bath and 2 hours at 20°–23° C. A minimum of methylene chloride (approximately 175 ml) is added to achieve a two-phase system. The organic layer is separated, dried over magnesium sulfate, filtered and reduced in volume under vacuum (less than 45° C.). Yield 48.5 g oxathiolane oxide (IV) in toluene.

The syrup containing oxathiolane oxide (IV) (prepared above) is heated at reflux with toluene (140 ml), p-toluenesulfonic acid monohydrate (0.036 g) and tetrabutyl ammonium bromide (0.7 g) under a Dean and Stark trap at 45°–47° C. at a pressure of about 80 mm Hg for 3 hours. Additional p-toluenesulfonic acid monohydrate (0.63 g) is added and the solution heated at a reflux temperature of 45°–47° C. for one hour followed by 75°–76° C. for 2½ hours.

The solution is cooled, washed with 10% sodium hydroxide (2×10 ml), water (10 ml), dried over magnesium sulfate and filtered. This material is then recrystallized from toluene. Yield (21.1 g) of oxathiin (V) 59% based on acetoacetanilide (II).

EXAMPLE 3

A mixture of toluene (50 ml), acetoacetanilide (35.4 g, 0.2 mole), 2-mercaptoethanol (14.4 ml, 0.203 mole, distilled) and p-toluenesulfonic acid monohydrate (0.5 g) is refluxed for 3½ hours under a Dean and Stark trap separated from the reaction vessel by a 12" Vigreux column. The solution is cooled and allowed to stand overnight. It is then stirred at 20°–23° C. with additional toluene (40 ml), saturated sodium bicarbonate (9 ml) and 10% sodium hydroxide (1 ml) for 25 minutes. Water (2 ml) containing sodium tungstate dihydrate (0.2 g) is added. The solution is cooled and treated dropwise with hydrogen peroxide (18.5 ml, 33.2%, 0.205 mole) at 2°–4° C. with vigorous stirring over 10 minutes. The solution is stirred in an ice bath for 2 hours and at 23°–25° C. for 2 hours. A minimum of methylene chloride (approximately 130 ml) is added. The organic layer is separated, dried over magnesium sulfate, filtered and reduced in volume under vacuum (45° C. or less). Yield 59.1 g. Conversion 93±2 mole percent from acetoacetanilide (II) to oxathiolane oxide (IV).

EXAMPLE 4

Example 1 is repeated, except that in place of starting with unsubstituted acetoacetanilide, the corresponding 2-methoxyphenyl body is used, to form 5,6-dihydro-N-(2-methoxyphenyl)-2-methyl-1,4-oxathiin-3-carboxamide in 46–50% yield based on the substituted acetoacetanilide.

EXAMPLE 5

Example 1 is repeated, except that in place of starting with unsubstituted acetoacetanilide, the corresponding 2-methylphenyl body is used, to form 5,6-dihydro-2-methyl-N-(2-methylphenyl)-1,4-oxathiin-3-carboxamide in 58% yield based on the substituted acetoacetanilide.

Table A summarizes a series of runs of Step A, the condensation reaction, identified as runs A-1 through A-7, using various solvents and conditions, with the results indicated. In Table A "pTSA" stands for p-toluenesulfonic acid monohydrate and "REACTANTS" stands for 2-mercaptoethanol plus acetoacetanilide. The yield and conversion are based on acetoacetanilide.

Table B summarizes a series of runs of Step B, the oxidation reaction, identified as runs B-1 through B-11. In Table B, "III" stands for the unoxidized oxathiolane; the column headed "Source III" identifies the run of Table A from which the oxathiolane was obtained. All runs in Table B are carried out in toluene solvent, except for run B-4, which is carried out in chloroform. The conversion is expressed as mole percent based on acetoacetanilide.

cases except run C-5, where the reaction solvent is n-butyl acetate, and run C-6 where the reaction solvent is chloroform. The quaternary salt is tetrabutylammonium bromide in all runs, except run C-7 where tetrapentylammonium iodide is used, and run C-8 where trimethylphenylammonium bromide is used. In runs C-5, C-6 and C-7 the reaction mixture is washed between Stages II and III with dilute hydrochloric acid (about 5%; 2×200 ml per gram mole). The solvent of

Table A

STEP A - CONDENSATION REACTION

| RUN | SOLVENT | REACTION TEMP. °C. | REACTION TIME HOURS | EXCESS 2-MERCAPTO-ETHANOL % | pTSA WT. % REAC-TANTS | CRUDE YIELD OF OXATHIOLANE III WT. % | CON-VERSION MOLE % | PURITY WT. % | ML SOL-VENT PER GRAM REAC-TANTS |
|---|---|---|---|---|---|---|---|---|---|
| A-1 | TOLUENE | 50–55 | 5.25 | 10 | 1.5 | 99 | 99.1 | 99.1 | 2.3 |
| A-2 | TOLUENE | 60–65 | 5.5 | 5.6 | 1.1 | 98.6 | 97.7 | — | 1.15 |
| A-3 | TOLUENE | 60 | 4.5 | 1.5 | 0.9 | NOT ISOLATED | 98.4 | — | 1 |
| A-4 | TOLUENE | 55–60 | 6.5 | 3.7 | 0.9 | NOT ISOLATED | 98.7 | — | 1 |
| A-5 | CHCl$_3$ | 60 | 4 | 1.1 | 1.2 | 95.2 | 98 | — | 1 |
| A-6 | ISO-PROPYL ACETATE | 58–61 | 4.5 | 1.1 | 1.2 | 100 | 99 | — | 1 |
| A-7 | TOLUENE | 50–60 | 6 | 10 | 1.5 | 98 | — | 100 | 1.3 |

TABLE B

STEP B - OXIDATION REACTION

| Run | Source III | ml Solvent Per Gram III | Sodium Formate Wt % III | NaHCO$_3$ (Sat'd) ml Per Gram III | NaOH (10%) ml Per Gram III | H$_2$O ml Per Gram III | Na$_2$WO$_4$·2H$_2$O Wt % III | Time Stage One (Hours) | Temp. Stage One (°C.) | Time Stage Two (Hours) | Temp. Stage Two (°C.) | Mole % Conversion |
|---|---|---|---|---|---|---|---|---|---|---|---|---|
| B-1 | A-2 | 1.5 | — | 0.2 | — | 0.04 | 0.4 | 2 | 0–5 | 2 | 20–25 | 94 |
| B-2 | A-2 | 1.5 | — | 0.2 | — | 0.04 | 0.4 | 2 | 0–5 | 2 | 20–25 | 96.5 |
| B-3 | A-2 | 1.5 | — | 0.2 | — | 0.04 | 0.4 | 2 | 0–5 | 2 | 20–25 | 96 |
| B-4 | A-5 | 0.66 | 2.2 | — | — | 0.26 | 0.4 | 2 | — | 2.5 | 22–24 | 90 |
| B-5 | A-4 | 1.3 | — | 0.25 | .03 | 0.04 | 0.4 | 2.3 | 5–11 | 1.5 | 20–25 | 97 |
| B-6 | A-3 | 1.9 | — | .25 | .02 | 0.04 | 0.4 | 2.1 | 2–4 | 2 | 23–25 | 94.9 |
| B-7 | A-1 | 3.1 | 1.7 | — | — | — | 1.0 | 2 | 0.4 | 2 | 20–23 | 95 |
| B-8 | A-7 | 1.5 | — | 0.2 | — | 0.04 | 0.4 | 2 | 0 | 2 | 25 | 97.8 |
| B-9 | A-7 | 1.5 | — | 0.2 | — | 0.04 | 0.4 | 2 | 0 | 2 | 25 | 96.2 |
| B-10 | A-7 | 1.5 | — | 0.2 | — | 0.04 | 0.4 | 2 | 0 | 2 | 25 | 95.1 |
| B-11 | A-7 | 1.5 | — | 0.2 | — | 0.04 | 0.4 | 2 | 0 | 2 | 25 | 94.7 |

Table C summarizes a series of runs of Step C, the ring expansion reaction, identified as runs C-1 through C-8. In Table C, "IV" stands for the oxathiolane oxide, and "III" stands for the unoxidized oxathiolane. The column headed "Source IV" identifies the run of Table B from which the oxide is obtained. "pTSA" stands for p-toluenesulfonic acid monohydrate. The solvent employed in the ring expansion reaction is toluene, in all purification is isopropyl alcohol in all cases except run C-4 where toluene is used for purification. The yield is based on acetoacetanilide.

The material obtained from Runs C-1 through C-8 was examined by proton magnetic resonance and high pressure liquid chromatography and found to be 5,6-dihydro-2-methyl-N-phenyl-1,4-oxathiin-3-carboxamide.

TABLE C

STEP C - RING EXPANSION REACTION

| RUN | SOURCE IV | ML SOLVENT PER GRAM III | QUATERNARY SALT WT % IV | STAGE ONE pTSA WT % III | STAGE ONE TIME HOURS | STAGE ONE TEMP. °C. | STAGE TWO pTSA WT % III | STAGE TWO TIME HOURS | STAGE TWO TEMP. °C. | STAGE THREE pTSA WT % III | STAGE THREE TIME HOURS | STAGE THREE TEMP. °C. | YIELD WT. % |
|---|---|---|---|---|---|---|---|---|---|---|---|---|---|
| C-1 | B-1 | 3.9 | 2 | 0.1 | 3 | 50 | 1.5 | 1 | 50 | — | 3 | 80 | 63 |
| C-2 | B-2 | 3.9 | 0.5 | 0.1 | 3 | 40–45 | 1.5 | 1 | 50 | — | 3 | 75 | 59.3 |
| C-3 | B-3 | 9 | 0.5 | 0.1 | 3 | 50 | 1.5 | 1 | 50 | — | 3 | 80–85 | 59 |
| C-4 | B-7 | 3.9 | 2 | 0.1 | 3 | 45–47 | 1.8 | 1 | 45–47 | — | 2.5 | 75–76 | 59 |
| C-5 | B-8 | 3.9 | 2 | 0.1 | 3 | 46–48 | 1 | 1 | 46–48 | 1.5 | 3 | 75–80 | 51.7 |
| C-6 | B-9 | 3.9 | 2 | 0.1 | 3 | 47 | 1 | 1 | 45–46 | 1.5 | 3 | 64 | 54 |
| C-7 | B-10 | 3.9 | 2 | 0.1 | 3 | 47–48 | 1 | 1 | 45–46 | 1.5 | 3 | 72–77 | 31.9 |

TABLE C-continued

| | | | STEP C - RING EXPANSION REACTION | | | | | | | | |
|---|---|---|---|---|---|---|---|---|---|---|---|
| | | | STAGE ONE | | | STAGE TWO | | | STAGE THREE | | |
| RUN | SOURCE IV | ML SOLVENT PER GRAM III | QUATERNARY SALT WT % IV | pTSA WT % III | TIME HOURS | TEMP. °C. | pTSA WT % III | TIME HOURS | TEMP. °C. | pTSA WT % III | TIME HOURS | TEMP. °C. | YIELD WT. % |
| C-8 | B-11 | 3.9 | 2 | 0.1 | 3 | 46–48 | 1.5 | 1 | 46 | — | 3 | 75–76 | 60.6 |

We claim:

1. A method of making 5,6-dihydro-2-methyl-N-phenyl-1,4-oxathiin-3-carboxamide comprising the steps of:
   (A) providing 2-methyl-N-phenyl-1,3-oxathiolane-2-acetamide;
   (B) bringing together the 2-methyl-N-phenyl-1,3-oxathiolane-2-acetamide and hydrogen peroxide under basic conditions, in the presence of a catalytic quantity of a suitable heavy metal compound oxidation catalyst effective to catalyze the oxidation of said 2-methyl-N-phenyl-1,3-oxathiolane-2-acetamide by the said hydrogen peroxide, in a liquid medium comprising water, or water plus at least one nonprotic organic liquid selected from the group consisting of (a) aromatic hydrocarbon solvent having a boiling point not greater than 145° C., (b) chlorinated hydrocarbon solvent having a boiling point not greater than 130° C., and (c) a solvent having a boiling point not greater than 130° C. which is an alkyl ester of an aliphatic carboxylic acid, and subjecting the resulting mixture while agitating to a temperature of from 0°–25° C., whereby 2-methyl-N-phenyl-1,3-oxathiolane-2-acetamide 3-oxide is formed;
   (C) bringing together the 2-methyl-N-phenyl-1,3-oxathiolane-2-acetamide 3-oxide and a catalytic quantity of a quaternary ammonium salt under acidic conditions in a nonprotic organic liquid as defined in step (B) above, and heating the mixture at a temperature of 45°–80° C. while removing evolved water of reaction, and thereafter recovering from the reaction mixture the thus formed 5,6-dihydro-2-methyl-N-phenyl-1,4-oxathiin-3-carboxamide.

2. A method as in claim 1 in which step (C) is carried out directly on the mixture resulting from step (B) without changing solvent.

3. A method as in claim 1 in which the 2-methyl-N-phenyl-1,3-oxathiolane-2-acetamide in step (A) is provided in the form of an in-situ reaction product of 2-mercaptoethanol and acetoacetanilide prepared in an organic solvent as specified in step (B).

4. A method as in claim 3 in which steps (A), (B) and (C) are carried out in the same organic solvent.

5. A method as in claims 1 or 4 in which the solvent is xylene, toluene, chloroform, isopropyl acetate or n-butyl acetate.

6. A method as in claim 1 in which, in step (B), the liquid medium comprises at least 10% water by weight.

7. A method as in claim 1 in which there is not more than 4 liters of liquid medium present per kilogram of said oxathiolane in step (B).

8. A method as in claim 1 in which the pH of the reaction mixture in step (B) is 8–9.

9. A method as in claim 1 in which the heavy metal compound is a metal salt of tungstic or molybdic acid.

10. A method as in claim 1 in which the quaternary ammonium salt is a quaternary ammonium halide.

11. A method as in claim 10 in which the quaternary ammonium halide is tetra n-butylammonium bromide, tetra n-pentylammonium iodide or trimethylphenylammonium bromide.

12. A method of making 2-methyl-N-phenyl-1,3-oxathiolane-2-acetamide 3-oxide comprising bringing together 2-methyl-N-phenyl-1,3-oxathiolane-2-acetamide and hydrogen peroxide under basic conditions in the presence of a catalytic quantity of a heavy metal compound oxidation catalyst in a liquid medium comprising water or water plus at least one nonprotic organic solvent liquid selected from the group consisting of (a) aromatic hydrocarbon solvent having a boiling point not greater than 145° C., (b) chlorinated hydrocarbon solvent having a boiling point not greater than 130° C., and (c) a solvent having a boiling point not greater than 130° C. which is an alkyl ester of an aliphatic carboxylic acid, and subjecting the resulting mixture while agitating to a temperature of from 0°–25° C., whereby 2-methyl-N-phenyl-1,3-oxathiolane-2-acetamide 3-oxide is formed.

13. A method of making 5,6-dihydro-2-methyl-N-phenyl-1,4-oxathiin-3-carboxamide comprising bringing together 2-methyl-N-phenyl-1,3-oxathiolane-2-acetamide 3-oxide and a catalytic quantity of a quaternary ammonium salt under acidic conditions in at least one nonprotic organic liquid selected from the group consisting of (a) aromatic hydrocarbon solvent having a boiling point not greater than 145° C., (b) chlorinated hydrocarbon solvent having a boiling point not greater than 130° C., and (c) a solvent having a boiling point not greater than 130° C. which is an alkyl ester of an aliphatic carboxylic acid, and heating the mixture at a temperature of 45°–80° C. while removing evolved water of reaction, and thereafter recovering from the reaction mixture the thus formed 5,6-dihydro-2-methyl-N-phenyl-1,4-oxathiin-3-carboxamide.

14. A method of making 5,6-dihydro-2-methyl-N-phenyl-1,4-oxathiin-3-carboxamide comprising the steps of:
   (A) preparing 2-methyl-N-phenyl-1,3-oxathiolane-2-acetamide by bringing together 2-mercaptoethanol and acetoacetanilide in a nonprotic organic solvent liquid selected from the group consisting of (a) aromatic hydrocarbon solvent having a boiling point not greater than 145° C., (b) chlorinated hydrocarbon solvent having a boiling point not greater than 130° C., and (c) a solvent having a boiling point not greater than 130° C. which is an alkyl ester of an aliphatic carboxylic acid, in the presence of p-toluenesulfonic acid or 2-napthalenesulfonic acid in amount sufficient to catalyze the condensation reaction of the 2-mercaptoethanol and acetoacetanilide, heating the reaction mixture to a temperature of 45°–70° C., and removing the water of condensation formed by said reaction, whereby 2-methyl-N-phenyl-1,3-oxathiolane-2-acetamide intermediate is formed;

(B) without recovery of the 2-methyl-N-phenyl-1,3-oxathiolane-2-acetamide from the reaction mixture of step (A), adding a base to the said reaction mixture to produce a pH within the range 8–9, and gradually adding aqueous hydrogen peroxide to the resulting basic mixture in the presence of a heavy metal compound oxidation catalyst selected from the group consisting of metal salts of tungstic acid, metal salts of molybdic acid and zirconium salts in an amount effective to catalyze the oxidation of the said oxathiolane intermediate by the hydrogen peroxide, and maintaining the mixture at a temperature of 0°–25° C. while agitating the mixture whereby 2-methyl-N-phenyl-1,3-oxathiolane-2-acetamide 3-oxide is formed;

(C) separating the organic phase of the mixture resulting from step (B), drying said organic phase, and without recovering the said 3-oxide adding to said organic phase p-toluenesulfonic acid or 2-naphthalenesulfonic acid and a quaternary ammonium halide selected from the group consisting of tetra n-butylammonium bromide, tetra n-pentylammonium iodide and trimethylphenylammonium bromide, in amounts sufficient to catalyze evolution of water and ring expansion of the said 3-oxide, heating the mixture at a temperature of 45°–80° C., and removing evolved water of reaction whereby the desired 5,6-dihydro-2-methyl-N-phenyl-1,4-oxathiin-3-carboxamide is formed.

15. A method as in claim 14 in which the said nonprotic organic solvent is (a) an aromatic hydrocarbon having a boiling point not greater than 143° C. and there is added to the reaction mixture at the conclusion of step (B) a quantity of methylene chloride equal to from 10 to 100% by volume of the reaction mixture prior to separating the organic phase for step (C).

16. A method as in claim 15 in which, after separating the said organic phase, the methylene chloride is evaporated prior to undertaking step (C).

17. A method as in claim 14 in which step (C) is carried out at a temperature within the range of 45°–50° C. until 30% of the theoretical quantity of water of reaction has been generated, and thereafter the reaction mixture is heated at a higher temperature of 75°–80° C.

18. A method as in claim 17 in which the reaction mixture is washed with dilute acid prior to heating at said higher temperature.

19. A method as in claim 14 in which the amount of liquid medium present is:
between 0.5 and 6 liters per kilogram of acetoacetanilide and mercaptoethanol in step (A);
between 0.5 and 4 liters per kilogram of said oxathiolane in step (B); and
between 1 and 6 liters per kilogram of said 3-oxide in step (C).

20. A method as in claim 14 in which the said solvent is toluene.

21. A method as in claims 14 or 20 in which the oxidation catalyst is sodium tungstate.

* * * * *